(12) United States Patent
Babalola et al.

(10) Patent No.: US 6,494,916 B1
(45) Date of Patent: Dec. 17, 2002

(54) APPARATUS FOR REPLACING MUSCULO-SKELETAL PARTS

(75) Inventors: Omotunde M. Babalola, Long Island, NY (US); Patrick R. Connelly, Rochester, NY (US); Stuart G. MacDonald, Pultneyville, NY (US)

(73) Assignee: Biomed Solutions, LLC, West Henrietta, NY (US)

( * ) Notice: Subject to any disclaimer, the term of this patent is extended or adjusted under 35 U.S.C. 154(b) by 0 days.

(21) Appl. No.: 09/918,068

(22) Filed: Jul. 30, 2001

(51) Int. Cl.[7] ................................................ A61F 2/36
(52) U.S. Cl. .................. 623/23.3; 623/23.26
(58) Field of Search ............................ 623/23.23, 23.3, 623/23.36, 23.42, 23.44, 23.46, 23.53, 23.11, 23.15, 23.19, 23.21, 23.22, 23.25, 23.48; 606/89, 76

(56) References Cited

U.S. PATENT DOCUMENTS

| | | | | |
|---|---|---|---|---|
| 4,728,335 A | * | 3/1988 | Jurgutis | 623/23 |
| 4,735,625 A | * | 4/1988 | Davidson | 623/16 |
| 4,892,550 A | * | 1/1990 | Huebsch | 623/22 |
| 4,936,859 A | * | 6/1990 | Morscher et al. | 623/18 |
| 5,180,395 A | * | 1/1993 | Klaue | 623/23 |
| 5,507,814 A | * | 4/1996 | Gilbert et al. | 623/16 |
| 5,593,445 A | * | 1/1997 | Waits | 623/18 |
| 5,876,446 A | * | 3/1999 | Agrawal et al. | 623/11 |
| 5,984,968 A | * | 11/1999 | Park | 623/18 |
| 6,290,726 B1 | * | 9/2001 | Pope et al. | 623/22.15 |

OTHER PUBLICATIONS

Yong San: Pub. No.: US 2001/0016780 A1.*

* cited by examiner

Primary Examiner—David H. Willse
Assistant Examiner—Javier S. Blanco
(74) Attorney, Agent, or Firm—Greenwald & Basch LLP; Howard J. Greenwald

(57) ABSTRACT

A prosthetic implant that contains a stem integrally connected to a neck, a head that sits on top of the neck, and a porous assembly disposed around them stem. The porous assembly contains a first porous tube and a second porous tube, wherein the second porous tube is disposed within the first porous tube, and the stem is disposed within the second porous tube. The porous assembly is a heat absorbent porous assembly which tends to maintain its temperature within a specified range.

12 Claims, 3 Drawing Sheets

APPARATUS FOR REPLACING MUSCULO-SKELETAL PARTS

FIELD OF THE INVENTION

An artificial prosthetic device comprised of a stem integrally connected to a neck portion, a head connected to the stem, and two porous tubes disposed about the stem.

BACKGROUND OF THE INVENTION

Defects of the joints, as a result of hip osteoarthritis, osteoporosis, trauma, occupational overuse, resection of cancerous tissue, and hip joint tumor are among the primary reasons for performing joint replacements. As one example, the hip joint is called a ball-and-socket joint because the spherical head of the thighbone (femur) moves inside the cup-shaped hollow socket (acetabulum) of the pelvis. In a properly functioning hip joint, a series of motions, such as flexion, extension, abduction and adduction, can be carried out to utmost capabilities without stress, strain or pain involved in the motions. After the onset of a hip or hip related diseases and/or fracture, there occurs a wear and tear of the joint and bones and the surrounding ligaments and tendons. This initiates an inflammatory response resulting in pain and swelling of the joint and surrounding tissue, leading to associated diseases and defects. In theses instances, hip replacement surgery is performed to alleviate the symptoms and replace the affected parts.

The use of prosthetic implants is the most successful method used in the cases of limb and joint replacement due to a number of diseases and/or accidents. Implants may be used in hip arthroplasty, total knee replacements, and prosthetic limbs. Hip prosthetics have a success rate of ninety percent for about twenty years, taking into account revision surgery. To duplicate the action of a normal functioning hip joint, a total hip replacement prosthetic implant must have three parts: the stem, which fits into the femur and provides stability; the ball, which replaces the spherical head of the femur and the acetabular cup, which replaces the worn-out hip socket. Each part comes in various sizes in order to accommodate various body sizes and types.

However, even with technological advancements in the design of prosthetic implants, there is still a significant amount of failure, resulting in pain, further damage of region surrounding implant, infection, recurrent arthritic condition and dislocation and the need for revision surgery leading to increase in expenses. U.S. Pat. No. 5,876,446 of Agrawal et al. discloses that "virtually all implants currently in use have a tendency to loosen with time, some to the extent of requiring revision." According to Agrawal et al., ". . . the absence of bone in-growth frequently leads to loosening of bone cemented prosthesis."

In order to solve this problem, Agrawal et al. provided a metallic press fit prosthetic device comprising at least one porous tissue mating surface on the metallic press fit prosthetic device having interstitial spaces impregnated with a polymer selected from a group consisting of polylactic acid (PLA), polyglutamic acid (PGA), and PLA-PGA copolymers The polymer contains a pharmacologically active substance whose release is controlled over a therapeutically effective period of time. The entire disclosure of U.S. Pat. No. 5,876,446 is hereby incorporated by reference into this specification.

Although the device of Agrawal et al. was an improvement over prior art devices, it still was deficient in certain respects. In the first place, it was not capable of delivering two or more pharmacologically active materials in timed sequence. It also lacked the ability to control the amount of friction produced at the joint and dissipate effectively, the heat produced in other parts of the prosthesis in vivo.

SUMMARY OF THE INVENTION

In accordance with this invention, there is provided a prosthetic implant comprised of a stem integrally connected to a neck, a head that sits on top said neck, and porous assembly disposed around the stem. The porous assembly is comprised of a first porous tube and a second porous tube, wherein the second porous tube is disposed within the first porous tube, and wherein the stem is disposed within the second porous tube. The porous assembly is a heat absorbent porous assembly which tends to maintain its temperature within a specified range. The head is comprised of means for releasing a material over a specified period of time.

BRIEF DESCRIPTION OF THE DRAWINGS

The invention will be described by reference to the following drawings, in which like numerals refer to like elements, and in which.

DESCRIPTION OF THE PREFERRED EMBODIMENTS

The invention relates to an implantable prosthesis, and in one embodiment, to a bone prosthesis that is attached to the bone and that provides improved methods for monitoring and responding to problems associated with the prosthesis in vivo.

In one embodiment, the prosthesis of this invention responds to changes in its characteristics and its environment, as would the biological element it is replacing.

Figure 1:
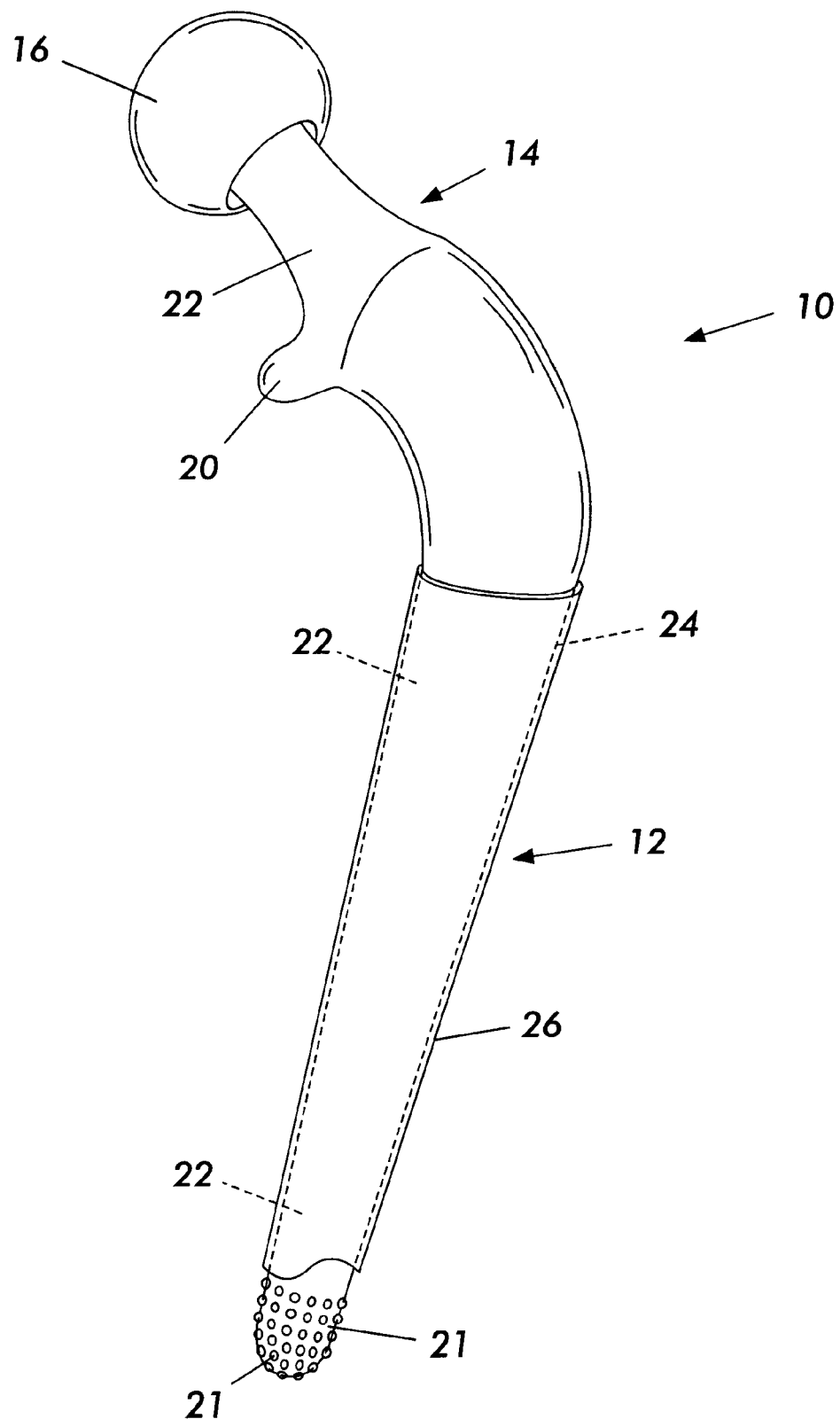
FIG. 1 is a schematic view of the implantable prosthesis of this invention.

The prosthesis of this invention may be used as a replacement for endogenously occurring musculoskeletal elements which have reduced or ceased in function, causing more harm than benefit. FIG. 1 is a schematic view of an implantable prosthesis 10 which, in the embodiment depicted, is a structure in the shape of femur but can also take the shape of a humerus, ulna, radius, and the like.

As is known to those skilled in the art, and referring to the embodiment depicted, the prosthesis 10 is properly referred to as a femoral implant. Reference may be had, e.g., to U.S. Pat. Nos. 5,766,261, 5,601,567, 5,231,611, 5,522,904, 5,376,125, 5,163,962, 5,179,877, and the like. The disclosure of each of these U.S. patents is hereby incorporated by reference into this specification.

Referring again to FIG. 1, femoral implant 10 is preferably an integral structure comprised of a stem section 12 and a neck section 14.

In the embodiment depicted in FIG. 1, the prosthesis 10 comprises a heat absorbent body 22. In another embodiment, not shown, heat absorbent body 22 is comprised of two metal alloys 18 which are joined together and which differ from each other in their material compositions and the heat absorbency.

The heat absorbent body 22 is capable of utilizing body heat to change one or more of its physical properties, such as its size and shape; and it additionally is capable of reverting to its original physical property, with the release of heat, when the ambient temperature to which it is exposed drops. Thus, in one embodiment, the heat absorbent body is capable of reverting to its original size and shape when the temperature of the organism in which it is disposed drops. In this embodiment, heat is first transformed into mechanical motion and is not transferred to the biological organism; and, thereafter, when the ambient temperature drops, heat then released to the biological organism while the material reverts to its original size and shape.

The ability of body 22 to change its shape upon being subjected to a temperature within a certain specified range is what is referred to as "heat absorbent" in this specification.

Those skilled in the art are well aware of heat absorbent alloy materials that may be made into articles which can be deformed from their original shape in to a different configuration that it heat unstable, i.e., that reverts to its original configuration upon the application of heat. Reference may be had, e.g., to International patent publication W0050100A1 of Boyle, the entire disclosure of which is hereby incorporated by reference into this specification.

By way of further illustration, and not limitation, the heat absorbent body 22 may be manufactured from spring steel or from alloys exhibiting super-elastic or shape memory properties. Articles manufactured from such alloys may be deformed from their original shape into a different configuration that is heat unstable, and upon the application of heat will revert to the original configuration. As disclosed in the aforementioned Boyle patent, certain shape memory alloys, including super-elastic nickel-titanium (NiTi) (nitinol) or copper-zinc-aluminum (CuZnAl) alloys that are well known in the art, can be deformed through the application of stress to the article of manufacture and will revert to their original shape upon removal of the stress in a phenomenon generally referred to as stress induced martensite (SIM), thereby eliminating the need for alternately cooling and heating the article. SIM shape memory alloys that are stressed at temperatures between where the alloy first begins to transform from austenite to martensite, and the maximum temperature at which martensite can occur, deform elastically up to a critical stress and then continue to deform through the formation of SIM. When the deforming stress is removed and the alloy is at a temperature above that which it starts to revert back to austenite, the alloy will attempt to return to its original shape. The temperature at which the alloy begin to revert to the stable austenite phase varies with the composition of the alloy, and, in one embodiment, it is preferable for the practice of the present invention that a SIM shape memory alloy be one that reverts back to austenite at the typical human body temperature of about 36.70 degrees Celsius.

Many different heat absorbent materials have been described in this specification. What they all have in common is that, at a specified temperature within the range from about 36 to about 38 degrees Centigrade, the material absorbs heat and changes at least one of its physical properties, such as its shape and/or the phase of one or more of its components. Additionally, when the ambient temperature drops below the aforementioned specified temperature within the range of from about 36 to about 38 degrees Centigrade, the material gives up heat and returns to its original physical state. Thus, the material tends to maintain the temperature area surrounding it at about the specified change temperature within the range of from about 36 to about 38 degrees Centigrade.

By way of illustration, the aforementioned materials of the Boyle patent will tend to maintain a substantially constant temperature by absorbing heat above about 36.7 degrees Centigrade (and changing phase) and releasing heat below about 36.7 degrees Centigrade and reverting to its original phase. Thus, this material tends to maintain the biological organism within which it is disposed within the narrow range of temperatures which sustain life.

Referring again to FIG. 1, the joined body is comprised of two metal alloys 18 located at the bottom of stem 12 and may be constructed of wear resistant titanium biocompatible alloy, as disclosed in U.S. Pat. No. 3,643,658 of Steinmann, of which the entire disclosure is hereby incorporated by reference into this specification. Other materials that are suitable as metal alloys 18 include biocompatible forms of copper-tin, copper-zinc, copper-zinc-tin, copper-zinc-xenon, copper-aluminum-nickel, copper-gold-zinc, gold-cadmium, gold-copper-zinc, iron beryllium ($Fe_3Be$), iron platinum ($Fe_3Pt$), indium-thalium, iron-manganese, iron-nickel-titanium-cobalt, nickel-titanium-vanadium, and silver-cadmium.

By way of further illustration and not limitation, one may use one or more of the heat absorbent materials described in U.S. Pat. Nos. 4,035,007, 4,144,057, 4,505,767, 4,894,100, 5,114,504, and 5,641,364. The entire disclosure of each of these U.S. patents is hereby incorporated by reference into this specification.

As is known to those skilled in the art, when the cells of living organisms are heated to a temperature in excess of about 45 degrees Fahrenheit, cell death occurs. Heat is often created by the frictional engagement of the prosthesis 10 with the bone it is disposed within. Such heat is preferably absorbed by the body 22, which utilizes the heat energy to change its shape, thereby dissipating the heat. In one preferred embodiment, the shape memory alloy 22 which comprises the heat-absorbing material has a heat capacity of 320 Joules per Kilogram-degree Celsius and a thermal conductivity of 600 Joules per meter-minute degree Celsius at high and low temperature phases.

The integral stress bearing region, comprised of alloy 18, joined to the absorbent body 22, will consist of pores 21 at the distal end of its stem to act as a means for increasing the anchorage of prosthesis 10, permitting in-growth of bone into the prosthesis 10.

In one preferred embodiment, the prosthetic implant will have a coating (not shown) on the entire length of the prosthetic implant 10. In another preferred embodiment, the coating (not shown) will be disposed on the portion (not shown) of the acetabular cup (not shown) in contact with living tissue. One may use, e.g., the coating described in U.S. Pat. No. 5,914,121 of Robey et al., the entire disclosure of which is hereby incorporated by reference into this specification. As is disclosed by Robey et al, the coating is combined from cultured human marrow stromal fibroblasts (MSFs) with hydroxyapatite/tri-calcium phosphate. The composition may further comprise fibrin glue. Preferably, the fibrin glue is derived from human fibrinogen when implanted into a human. Conversely, the use of human fibrinogen is preferable for implantation of human MSFs into humans because such fibrinogen can be easily isolated from blood of the individual undergoing implantation and will not induce an autoimmune reaction. In a preferred embodiment, MSFs are derived from human bone aspirates. In a preferred embodiment, from about $1\times10^5$ to $1\times10^8$ MSFs are loaded per 10 to 100 mg of delivery vehicle which in this case is stem 12. The hydroxyapatite/tri-calcium phosphate (HA/TCP) powder is washed with culture medium prior to combining with the MSF cell suspensions. After mixing, the MSFs-HA/TCP is incubated with rotation at about 37° C. for 40 to 90 minutes. In another preferred embodiment, fibrinogen is added to the MSF-loaded HA/TCP followed by thrombin. The resulting fibrin serves as a "glue" to hold the HA/TCP particles together.

In another embodiment, the prosthetic implant 10 will have a longitudinal pocket (not shown in FIG. 1, but see FIG. 4) running the length of the stem 12 between the core material 22 and the tubes 24/26.

Referring again to FIG. 1, and in the preferred embodiment depicted therein, it will be seen that heat absorbent body 22 is disposed, at least in part, within a tube 24 which encloses such body 22. In one embodiment, the material which comprises body 22 is preferably in a particulate form; and thus a tube 24 and a tube 26 is necessary to enclose it and to give it a defined shape.

It is preferred that tube 24 be made from a flexible, biocompatible material that is adapted to release a pharmacologically active material.

In one preferred embodiment, the tube 24 is made from one or more of the polymers disclosed in U.S. Pat. No. 5,876,466 of Agrawal et al., the entire disclosure of which is hereby incorporated by reference into this specification. These polymer materials may include, e.g., polylactic acid (PLA), poly (gamma-glutamic) acid (PGA), and PLA-PGA copolymers. These polymers preferably have a molecular weight of from about 40 to about 100,000 Kilo Daltons and preferably contain a pharmacologically active substance whose release is controlled over a therapeutically effective period of time when the prosthesis 10 is implanted.

As is disclosed in the Agrawal patent, the pharmacologically active substance may be an antibiotic. Alternatively, or additionally, the active substance may be: (1) an anti-infective agent, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethazine, sulfadiazine, sulfamerazine, sulfamethizole and sulfisoxazole; antiviral, including idoxuridine; and other anti-infective including nitrofurazone and sodium propionate; (2) an anti-allergenic agent, such as antazoline, methapyrilene, chlorpheniramine, pyrilamine and prophenpyridamine; (3) an anti-inflammatory agent, such as hydrocortisone, cortisone, dexamethasone 21-phosphate, fluocinolone, triamcinolone, medrysone, prednisolone, prednisolone 21-phosphate, and prednisolone acetate; (4) an estrogen based agent, such as estrone, 17β-estradiol, ethinyl estradiol, and diethyl stilbestrol; (5) a progestational agent, such as progesterone, 19-norprogesterone, norethindrone, megestrol, melengestrol, chlormadinone, ethisterone, medroxyprogesterone, norethynodrel and 17.alpha.-hydroxyprogesterone; (6) a humoral agent, such as the prostaglandins, for example, $PGE_1$, $PGE_2$, and $PGF_2$; (7) an antipyretic agent, such as aspirin, sodium salicylate, and salicylamide; (8) a nutritional agent, such as essential amino acids and essential fats; and (9) an osteoinductive agent; and the like. Other drugs having the same or different activity as those recited above can be employed in drug-delivery systems within the scope of the present invention.

Referring again to FIG. 1, and in the preferred embodiment depicted therein, it will be seen that tube 24 acts as one drug delivery system in the prosthesis 10 of the invention. Tube 24 is disposed within a similar tube 26, which also is made from a biodegradable material such as PLA, PGA, and PLA-PGA copolymers. Tube 26 may delivery the same agent as tube 24 at the same rate, and/or it may deliver one or more different agent(s) at one or more different rates.

In one preferred embodiment, the prosthetic implant 10 will have porous tubes 24 and 26 along its stem 12 for the timed release of antibiotic and anti-inflammatory drugs, fibroblast, osteoblast and morphogens; these and other agents are described in U.S. Pat. No. 5,453,235 of Calcote et al, the entire disclosure of which is hereby incorporated by reference into this specification. Disclosed in this patent is a dual porosity polytetrafluoroetylene (PTFE) tube 24 and 26 including an inner surface of expanded PTFE material in tubular form having a first porosity and an outer surface of expanded PTFE material in tubular form having porosity different from that of the first surface. The porosity of the inner surface and the porosity of the outer surface are both within a range of about 0.01–200 microns. The preferred method of making a dual porosity PTFE tube includes the step of forming an inner preformed tubular billet and an outer preformed tubular billet; the outer billet is adapted to closely fit concentrically within the inner billet. Porosity of the inner and outer surfaces is varied within a range of about 0.1–150 microns by changing, in the respective billet, the lubrication level and/or PTFE resin particle size. The preferred fluoropolymer, PTFE, is chosen due to its low coefficient of friction, but is by no means limited to it.

In one preferred embodiment, the inner surface of the PTFE tube is made less porous to reduce blood leakage, while the outer surface is made more porous to enhance tissue ingrowth. In another embodiment, the aforementioned porosity is reversed, that is, the inner surface is made more porous while the outer surface is made less porous, to accelerate healing of bone into the prosthetic implant.

In one preferred embodiment, the method for protecting mammalian tissue from damage associated with an inflammatory response following a tissue injury is as described in U.S. Pat. No. 6,194,376 by Kuberasampath et al, the entire disclosure of which is hereby incorporated by reference into this specification. The method of this patent makes use of osteogenic protein 1 (OP-1), which is known by those skilled in the art as a tissue morphogens. It is a substance competent to induce tissue-specific morphogenesis of mammalian body tissue in addition to bone and/or cartilage; and it provides a method for treating and protecting mammalian tissue from damage associated with the inflammatory response following injury. It also provides a method for alleviating tissue damage associated with immune cell mediated inflammatory response, ischemia-reperfusion, hyperoxia or hypoxia injury and tissue by administering a morphogen other than a TGF-$\beta_2$, to tissue affected by an immune cell mediated response, said morphogen comprising a dimeric protein having an amino acid sequence.

Figure 4:
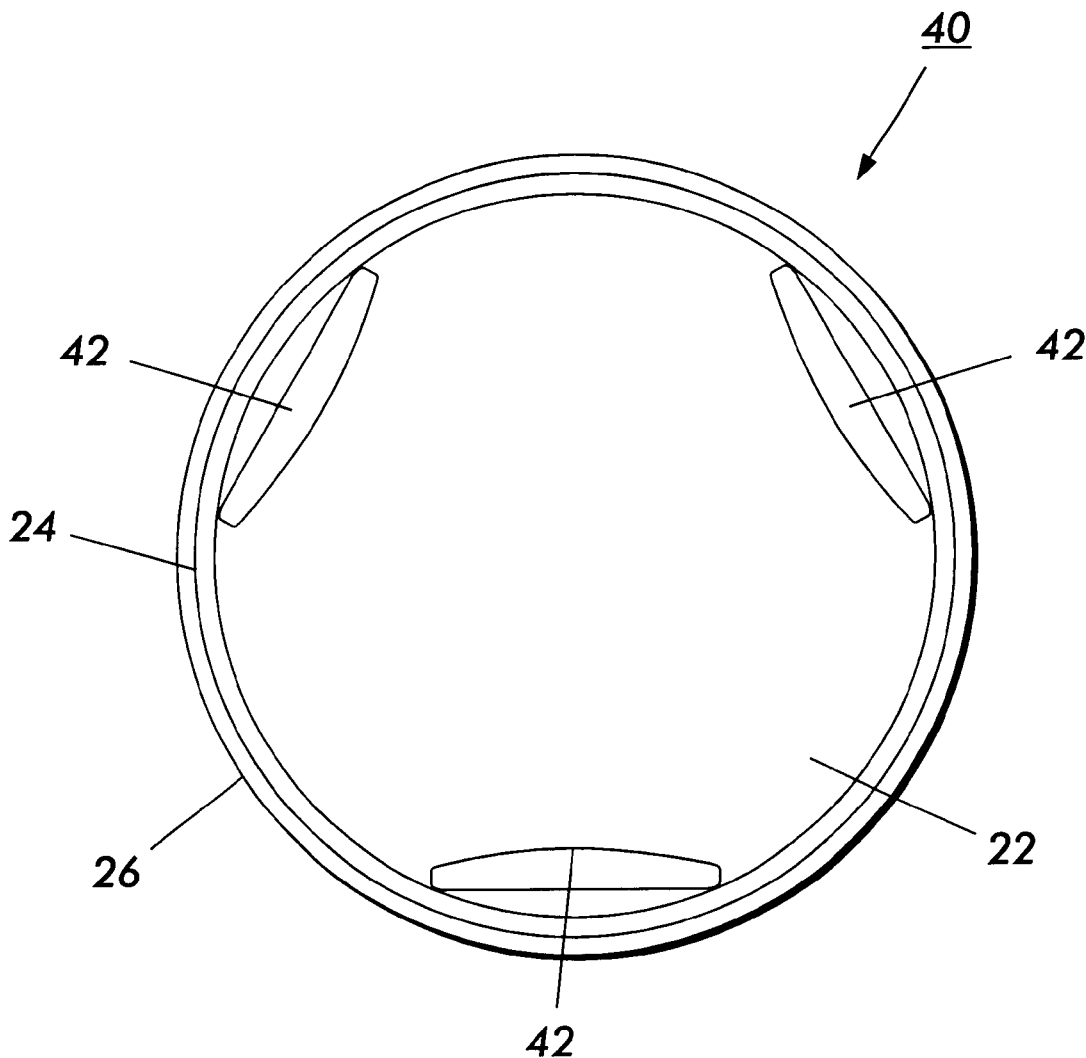
FIG. 4 is a sectional view of the stem of the prosthesis of FIG. 1.

In another embodiment, as depicted in FIG. 4, the absorbent body 22 has invaginations 42 of depth not exceeding fifty percent of the cross-sectional area of the implant 10. This provides for rigid placement into the organism, immobilizing the implant further.

In another embodiment, not shown, the aforementioned invaginations 42 contain nanoporous biocompatible membrane in the shape of a sac. Such membrane contains time releases drugs. By way of illustration, one may use the nanoporous biocompatible membrane described by the World organization patent number 9,855,101A1.

The biocompatible nanoporous membrane disclosed in the aforementioned World organization patent number 9,855,101A1 enables sustained delivery of drugs over weeks to months. The controlled pore size of the membrane can be as small as 1 nanometer up to more than 250 nanometers, with over 100 million pores per square centimeter and a thickness of 100 micro-meters. By use of a controlled nanoporous membrane, the drug can be delivered from an implantable system over several weeks to several months. The delivery profile can be tailored to specific pharmacokinetic requirements by modification of the size as well as the thickness of the membrane. Additional surface chemistry can be added to the membrane in order to delay the delivery over a prolonged period of time. The number of pores can be as high as one billion pores per square centimeter. The thickness of the membrane can be between 50 nanometers and several hundreds of micrometers.

Figure 2:
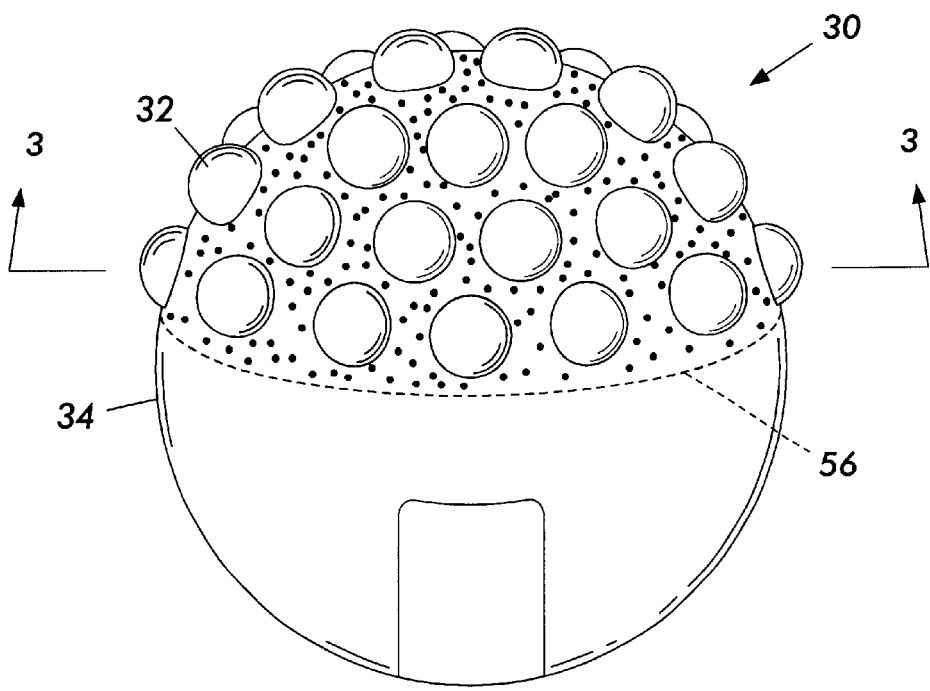
FIG. 2 is a schematic view of the head of the implantable prosthesis of this invention; (also the release of lubrication)
Figure 3:
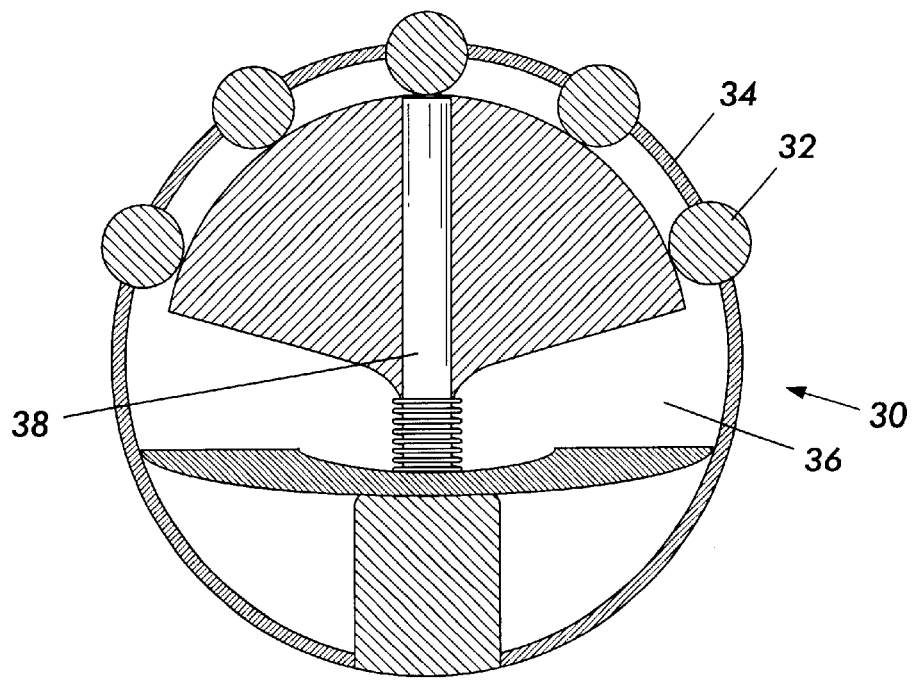
FIG. 3 is a sectional view of the head of the prosthesis of FIG. 2.

In one preferred embodiment, depicted in FIGS. 2 and 3, the head 30 of the prosthetic implant is configured in such a manner that such head 30 consists of solid circular shaped objects 32, a load bearing spring system 38, a circular shaped shell enclosing the entire system 34 comprising said bearing system 38.

In another preferred embodiment, depicted in FIGS. 2 and 3, the solid circular shaped objects 32, which might be in contact with a naturally occurring surface within the body (such as, e.g., calcified bone), will have a preferred coating of diamond-like carbon disposed on them.

As is apparent to those skilled in the art, and as is disclosed in U.S. Pat. No. 6,010,533 of Pope et al. (the entire disclosure of which is hereby incorporated by reference into this specification), the primary problem with prosthetic joint today is that the joints eventually erode and must be replaced. This erosion is caused, in large part, by the forces of impact and function routinely encountered by the load-bearing surfaces of the prosthetic joint. As the joint is repeatedly used, the elements of the joint wear against each other and the impact and friction forces eventually cause pieces if the load bearing surfaces to spall and float above the joint. This debris initiates a hystiocytic reaction in which the body's immune system is activated and releases enzymes to dissolve the particles. However, because the debris is usually relatively hard material, such as metal or polycarbon compounds, the enzymes usually fail to dissolve the debris, or take a considerable amount of time to do so. To further complicate matters, the enzymes react with the bone supporting the prosthetic joint. The enzymes weaken or dissolve the bone. This condition causes osteolysis or weakening of the bone, therefore weakening attachment to the bone and making it difficult to replace the prosthetic joint when the beating surfaces have eroded to such a point that the joint should be replaced. Osteolysis decreases the lifetime of the replacement prosthetic joint, and eventually renders the bone unusable. The entire disclosure of this U.S. Pat. No. 6,010,533 is hereby incorporated by reference into this specification. Disclosed in this patent is a method of making a prosthetic joint having load bearing surfaces which interact to enable rotation of one of the load-bearing surfaces relative to one another, the method comprising the steps of coating at least one of the load bearing surface with polycrystalline diamond compact having particles with a common diameter ranging form one nanometer to 100 microns. The method also comprises the step of polishing the diamond layer to an RA value of between 0.1 and 0.010 microns to a high luster to provide the diamond layer a low coefficient of friction.

In another preferred embodiment, the coating material of the circular shaped shell enclosing the entire system 34 is either polycrystalline diamond compact or some form of biocompatible titanium alloy, as is described in U.S. Pat. No. 6,010,533 by Pope et al.

In this embodiment, the circular solid objects 32 act as a buffer between a lubrication liquid and the acetabular component or the naturally occurring surface within the body it's in contact with (see FIG. 3).

In another embodiment, the lubrication dispensed within the cavity of the circular shaped shell 36 can be of a saline solution, such as phosphate buffered solution, ringers solution (which contains sodium chloride, potassium chloride, calcium chloride, sodium bicarbonate and glucose in the concentrations in which they occur in body fluids) and phospholipids. Such phospholipids include those as described in U.S. Pat. No. 6,133,249 by Hills et al. The patent provides phospholipids and propylene glycol based lubricants to be administered to physiological joints, articulations and prosthetic or partly prosthetic joints. The composition comprises between about 25 milligrams to about 500 milligrams of phospholipids per 1 milliliter of propylene glycol administered at a volume of between 0.1 milliliter to about 10 milliliters. One or more of the phospholipids are selected from a group consisting of shingolipids, phosphoglycerides, phosphatidylcholine, phosphatidylethanolamine, phosphatidylserine, phosphatidylglycerol, phosphatidylinositol, sphingomyelin and derivatives thereof which are suitable in lubricant compositions where in said phospholipids is a alpha-dipalmitoyl phosphatidylcholine, racemic alpha-dipalmitoyl phosphatidylcholine or a L-enantiomeric alpha-dipalmitoyl phosphatidylcholine.

Without wishing to be bound to any particular theory, applicants believe that the combined effect of balls and bearing system (of the diamond coated solid circular shaped objects 32) and lubricant dispensed within the cavity of the head 36 (as shown in FIG. 3) produces a synergistic friction reducing effect.

It should be noted that the methods and ideas described in this patent are not limited in use to hip joints, but can also be incorporated into other joints of the body and portions of the bone where use of a prosthetic implant is required for the treatment of a bone related disease or injury.

We claim:

1. A prosthetic implant comprised of a stem integrally connected to a neck, a head that sits on top of said neck, and a porous assembly disposed around said stem, wherein:
    a. said porous assembly is comprised of a first porous tube and a second porous tube, wherein said second porous tube is disposed within said first porous tube, and wherein said stem is disposed within said second porous tube,
    b. said porous assembly is a heat absorbent porous assembly, and
    c. said head is comprised of a load bearing spring system.

2. A prosthetic implant comprised of a stem integrally connected to a neck, a head that sits on top of said neck, and a porous assembly disposed around said stem, wherein:
    a. said porous assembly is comprised of a first porous tube and a second porous tube, wherein said second porous tube is disposed within said first porous tube, and wherein said stem is disposed within said second porous tube,
    b. said porous assembly is a heat absorbent porous assembly, and
    c. said heat absorbent porous assembly is comprised of a shape memory alloy.

3. A prosthetic implant comprised of a stem integrally connected to a neck, a head that sits on top of said neck, and a porous assembly disposed around said stem, wherein:

a. said porous assembly is comprised of a first porous tube and a second porous tube, wherein said second porous tube is disposed within said first porous tube, and wherein said stem is disposed within said second porous tube, b. said porous assembly is a heat absorbent porous assembly, and c. said heat absorbent porous assembly is comprised of heat absorbent material and, at a temperature within the range of from about 36 to about 38 degrees Centigrade, said heat absorbent material absorbs heat and changes one of its physical properties.

4. The prosthetic implant as recited in claim 3, wherein said heat absorbent porous assembly is comprised of two metal alloys which are joined together.

5. The prosthetic implant as recited in claim 3, wherein said stem is comprised of a bottom portion.

6. The prosthetic implant as recited in claim 5, wherein said bottom portion is comprised of a titanium alloy.

7. The prosthetic implant as recited in claim 5, wherein said bottom portion is comprised of a multiplicity of pores.

8. prosthetic implant as recited in claim 3, wherein said prosthetic implant is comprised of a coating.

9. The prosthetic implant as recited in claim 3, wherein said first porous tube consists essentially of a biodegradable material.

10. The prosthetic implant as recited in claim 9, wherein said second porous tube consists essentially of a biodegradable material.

11. The prosthetic implant as recited in claim 3, wherein said head is comprised of a multiplicity of solid, circular shaped objects.

12. A prosthetic implant comprised of a stem integrally connected to a neck, a head that sits on top of said neck, and a porous assembly disposed around said stem, wherein:

a. said porous assembly is comprised of a first porous tube and a second porous tube, wherein said second porous tube is disposed within said first porous tube, and wherein said stem is disposed within said second porous tube, b. said porous assembly is a heat absorbent porous assembly, and c. said head is comprised of a multiplicity of solid, circular shaped objects that comprise a carbon coating disposed on the exterior surfaces of said objects.

* * * * *